(12) United States Patent
Bontus et al.

(10) Patent No.: US 7,403,587 B2
(45) Date of Patent: Jul. 22, 2008

(54) COMPUTER TOMOGRAPHY METHOD USING A CONE-SHAPED BUNDLE OF RAYS

(75) Inventors: Claas Bontus, Hamburg (DE); Thomas Köhler, Norderstedt (DE); Michael Grass, Bucholz in der Nordheide (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 162 days.

(21) Appl. No.: 10/570,088

(22) PCT Filed: Aug. 23, 2004

(86) PCT No.: PCT/IB2004/051523
§ 371 (c)(1), (2), (4) Date: Mar. 1, 2006

(87) PCT Pub. No.: WO2005/023114
PCT Pub. Date: Mar. 17, 2005

(65) Prior Publication Data
US 2007/0019776 A1  Jan. 25, 2007

(30) Foreign Application Priority Data
Sep. 5, 2003  (EP)  ................... 03102708

(51) Int. Cl.
*A61B 6/03* (2006.01)
(52) U.S. Cl. ............................ 378/4; 378/15
(58) Field of Classification Search .......... 378/4, 378/210, 901, 15
See application file for complete search history.

(56) References Cited

U.S. PATENT DOCUMENTS

| | | | |
|---|---|---|---|
| 5,187,659 A * | 2/1993 | Eberhard et al. | 378/9 |
| 5,278,884 A * | 1/1994 | Eberhard et al. | 378/4 |
| 5,375,156 A * | 12/1994 | Kuo-Petravic et al. | 378/9 |
| 5,611,026 A | 3/1997 | Eberhard et al. | 395/119 |
| 5,887,047 A | 3/1999 | Bailey et al. | 378/4 |

(Continued)

FOREIGN PATENT DOCUMENTS

JP  2001145621 A * 5/2001

OTHER PUBLICATIONS

Kohler et al., Evaluation of Helical Cone-Beam CT Reconstruction Algorithms, Nov. 10-16, 2002, Nuclear Science Symposium Conference Record, 2002 IEEE, vol. 2, pp. 1217-1220.*

(Continued)

*Primary Examiner*—Chih-Cheng G Kao
*Assistant Examiner*—John M Corbett (57) ABSTRACT

The invention relates to a computer tomography method in which an examination area is passed through by a cone-shaped bundle of rays. The bundle of rays comes from a radiation source location which moves around the examination area on an overall trajectory. The overall trajectory consists of a first, closed partial trajectory, at least one second, closed partial trajectory and at least one third partial trajectory which connects the first and the at least one second partial trajectories to one another. Measured values which depend on the intensity in the bundle of rays on the other side of the examination area are acquired by means of a detector unit while the radiation source location is moving on the overall trajectory, and a CT image of the examination area is reconstructed from these measured values.

20 Claims, 7 Drawing Sheets

U.S. PATENT DOCUMENTS

| | | | | |
|---|---|---|---|---|
| 6,014,419 | A | 1/2000 | Hu | 378/4 |
| 6,018,561 | A | 1/2000 | Tam | 378/4 |
| 6,084,937 | A | 7/2000 | Tam | 378/4 |
| 6,275,560 | B1 * | 8/2001 | Blake et al. | 378/8 |
| 6,324,245 | B1 | 11/2001 | Tam | 378/4 |
| 6,330,298 | B1 | 12/2001 | Tam | 378/4 |
| 6,426,989 | B2 * | 7/2002 | Grass et al. | 378/4 |
| 6,459,756 | B1 | 10/2002 | Tam et al. | 378/15 |
| 6,504,892 | B1 | 1/2003 | Ning | 378/4 |
| 6,580,777 | B1 * | 6/2003 | Ueki et al. | 378/17 |
| 2003/0161444 | A1 * | 8/2003 | Katsevich | 378/210 |

OTHER PUBLICATIONS

Grass et al., 3D cone-beam CT reconstruction for circular trajectories, 2000, Phys. Med. Biol., vol. 45, pp. 329-347.*

Kachelriess, M., et al.; Kymogram detection and kymogram-correlated image reconstruction from subsecond spiral comp. Tom. scans of the heart; 2002; Med. Phys.; 29(7)1489-1503.

Kak/Slaney, eds.; Algebraic Reconstruction Technique (ART), Chpt. 7-Algebraic Reconstruction Algorithms; 1988; IEEE Press; pp. 275-296.

Katsevich, A.; Analysis of an exact inversion algorithm for spiral cone-beam CT; 2002; Phys. Med. Biol.; 47:2583-2597.

Tam, K.C., et al.; Exact (Spiral + Circles) Scan Region-of-Interest Cone Beam Reconstruction Via Backprojection; 2000; IEEE Trans. On Med. Imaging; 19(5)376-383.

Tang, X., et al.; An Efficient Cone Beam Filtered Back-projection (CB-FBP) Reconstruction Algorithm for a Circle-plus-two-arc Orbit; 2001; IEEE;15-126-5-130.

* cited by examiner

COMPUTER TOMOGRAPHY METHOD USING A CONE-SHAPED BUNDLE OF RAYS

The invention relates to a computer tomography method in which an examination area, in which a patient may be located, is irradiated by a cone-shaped bundle of rays and a radiation source which emits the bundle of rays moves relative to the examination area. Measured values which depend on the intensity of the radiation transmitted through the examination area are acquired by a suitable detector unit, and a CT image of the examination area is reconstructed from these measured values. Moreover, the invention relates to a computer tomography scanner for carrying out the method and to a computer program for controlling the computer tomography scanner.

In known methods of the type mentioned above, the radiation source location of the radiation source, that is to say the location from which the bundle of rays comes, moves relative to the examination area on a circular or helix-like trajectory. The circular trajectory has the disadvantage that the regions of the examination area which do not lie in the plane of the trajectory cannot be reconstructed using exact methods. Although these regions can be reconstructed using approximative methods, this leads to artefacts in the CT images. In this connection, a data record acquired along a circular trajectory is not complete. A data record is complete when, for each point in the examination area that is to be reconstructed, each plane containing this point intersects the trajectory at least once, and when this point is passed through by rays which come from at least one of these points of intersection and the absorption of these rays is measured.

If, on the other hand, the radiation source location moves on a helix-like trajectory during the acquisition, the acquired measured values are complete and the examination area can be reconstructed using exact reconstruction methods, for example using the reconstruction method published in the article "Analysis of an exact inversion algorithm for spiral cone-beam CT", A. Katsevich, Phys. Med. Biol. 47, 2583-2597, 2002 (E1). One disadvantage in the case of a helix-like trajectory is that during the acquisition the radiation source location assumes each position on the trajectory only once, since the radiation source or the radiation source location continuously advances relative to the examination area in the direction of the axis of rotation. Measured values which cannot be used for the acquisition on account of acquisition errors or movements of the object that is to be examined are therefore not measured again. In the case of periodically moving objects in which rest phases, in which the object hardly moves, and movement phases, in which the object moves a great deal, alternate, such as in the case of the heart for example, only measured values which have been acquired during the rest phases are used for reconstruction. Since the radiation source advances relative to the examination area in the direction of the axis of rotation, measured values are often acquired over too small an angular range, or simply too few measured values at a point of the axis of rotation are acquired, so that a reconstruction of a slice image at these points is not possible with sufficient quality.

It is an object of the present invention to specify a method, a computer tomography scanner and a computer program in which the abovementioned problems are reduced, so that a CT image of better quality can be reconstructed.

According to the invention, this object is achieved by a computer tomography method comprising the following steps:

producing a cone-shaped bundle of rays by means of a radiation source, said bundle of rays passing through an examination area and coming from a radiation source location, producing a relative movement between the radiation source location on the one hand and the examination area on the other hand along an overall trajectory, wherein the relative movement comprises a rotation about an axis of rotation along a first, closed partial trajectory, a rotation about the axis of rotation along at least one second, closed partial trajectory and a movement along at least one third partial trajectory which connects the first and the at least one second partial trajectories to one another, acquiring measured values which depend on the intensity in the bundle of rays on the other side of the examination area, by means of a detector unit during the relative movement, reconstructing a CT image of the examination area from the measured values.

For each point of the examination area that is to be reconstructed between the first and the second partial trajectory, each plane containing this point intersects the overall trajectory at least once. It is thus possible with this overall trajectory, unlike in the case of a circular overall trajectory, to acquire a complete data record if the respective point is passed through by rays which come from at least one of the respective points of intersection. The examination area which lies between the first and the at least one second partial trajectory can thus be reconstructed using exact reconstruction methods, and this leads to an improved image quality.

Furthermore, the radiation source location can, unlike in the case of the helix-like trajectory, rotate along the first and the at least one second trajectory about the axis of rotation until a sufficient amount of measured values to reconstruct the trajectory planes has been acquired. This leads, particularly in the case of the reconstruction of periodically moving objects of the abovementioned type such as the heart for example, to an improved image quality since the radiation source location can rotate relative to the examination area along the first and the at least one second trajectory until a desired amount of measured values which correlate with a rest phase of the object has been acquired for the reconstruction. As described above, this is not possible with a radiation source location which moves along a helix-like trajectory.

As claimed in claim 2, the third partial trajectory is also closed so that the radiation source location can also rotate along this partial trajectory until a desired amount of measured values has been acquired for the reconstruction. This leads to a further improvement in image quality.

The movement of the radiation source location relative to the examination area on closed partial trajectories allows simpler technical implementation of the movement since no reversal of the rotation movement of the radiation source is required and in particular the radiation source can rotate with a constant angular velocity.

As claimed in claim 3, the first and the at least one second partial trajectory in each case form a circle, which makes it possible to further simplify implementation of the method by means of a computer tomography scanner and leads to a reduced computational complexity during the reconstruction.

Claim 4 describes a reconstruction using a filtered back-projection, which leads to a further improvement in the image quality while having a low degree of computational complexity.

A further improvement in image quality can be achieved with the embodiments as claimed in claims 5 and 6.

In the embodiment as claimed in claim 7, if a periodically moving object is located in the examination area, measured values are essentially acquired only when the object is in a rest phase. In this case, the radiation source location moves along the first and the at least one second partial trajectory until the radiation source locations on the first and the at least one second trajectory that belong to the acquired measured values have scanned a predefined angular range or predefined angular ranges. These angular ranges may be selected such that a periodically moving object can be reconstructed with good image quality. They may be selected, for example, such that from each point in the examination area that is to be reconstructed the radiation source location can be seen during the rest phases over a continuous or total angular range of 180°.

Claim 8 provides that a dynamic collimator arrangement collimates the cone-shaped bundle of rays such that for each radiation source location the cone-shaped bundle of rays is delimited by two adjacent partial trajectories selected from the first and the at least one second partial trajectory. This leads, for example, in respect of a human patient, to a reduction of the exposure to radiation.

A computer tomography scanner for carrying out the method according to the invention is described in claim 9. The embodiment as claimed in claim 10 allows a movement of the radiation source location of the radiation source, in particular a focal spot of an X-ray source, and thus a movement of the radiation source location relative to the examination area along the at least one third partial trajectory, without an object located in the examination area having to be moved in the direction of the axis of rotation, for example by moving a patient table. The acquisition process is therefore more pleasant for a patient, and an undesired movement of a patient relative to a patient table becomes more unlikely, so that the image quality is further improved. Since the focal spot of an X-ray source can be moved more quickly than a physical object, this preferred embodiment furthermore leads to more rapid acquisition of the measured values.

The preferred embodiment of a computer tomography scanner as claimed in claim 11 allows the detection and recording of the movement of an object. It is thus possible to acquire measured values essentially only when the object is in a rest phase or to use for reconstruction only measured values which have been acquired during a rest phase. This leads to a further improvement in image quality.

As claimed in claim 12, the computer tomography scanner has a dynamic collimator arrangement which is adapted such that for each radiation source location the cone-shaped bundle of rays is delimited by two adjacent partial trajectories selected from the first and the at least one second partial trajectory. As mentioned above, this leads to a reduction in the exposure to radiation.

Claim 13 defines a computer program for controlling a computer tomography scanner as claimed in claim 9.

The invention will be further described with reference to examples of embodiments shown in the drawings to which, however, the invention is not restricted.

Figure 1:
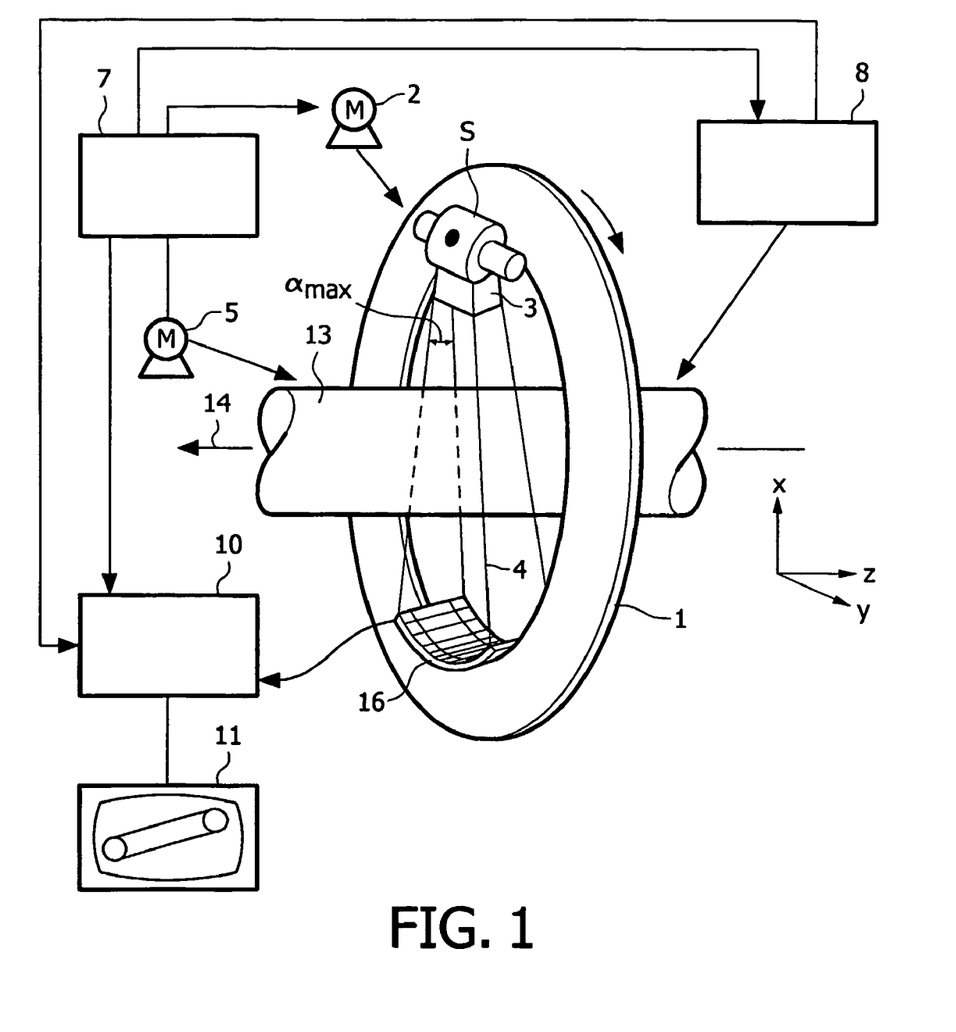
FIG. 1 shows a computer tomography scanner according to the invention which can be used to carry out the method according to the invention.

The computer tomography scanner shown in FIG. 1 comprises a gantry 1 which can rotate about an axis of rotation 14 that runs parallel to the z direction of the coordinate system shown in FIG. 1. For this purpose, the gantry 1 is driven by a motor 2 at a preferably constant but adjustable angular velocity. Attached to the gantry 1 is a radiation source S, for example an X-ray source. The latter is provided with a collimator arrangement 3 which screens out, from the radiation generated by the radiation source S at the radiation source location, a cone-shaped bundle of rays 4, that is to say a bundle of rays which has a finite extent other than zero both in the z direction and in a direction perpendicular thereto (that is to say in a plane perpendicular to the axis of rotation 14).

The bundle of rays 4 penetrates a cylindrical examination area 13 in which a periodically moving object (not shown) is located in this embodiment according to the invention. This object is in this case a beating heart which carries out intrinsic movements and under some circumstances is also moved back and forth on account of breathing movements of the patient. In other embodiments, non-moving objects or other periodically moving body organs such as the liver or brain, periodically moving parts of body organs or periodically moving technical objects may also be irradiated. The computer tomography method according to the invention can also be carried out when an object which is not moving is located in the examination area 13. Furthermore, objects within which other objects are moving may be irradiated. For example, the propagation of a contrast agent in the human body can be observed using the computer tomography scanner (perfusion examination). For this purpose, the body is generally irradiated over a relatively long period of time with low-dose radiation.

Once it has passed through the examination area 13, the bundle of rays 4 impinges on a detector unit 16 which is attached to the gantry 1 and has a detector surface that comprises a large number of detector elements, said detector elements being arranged in rows and columns in the manner of a matrix in this embodiment. The detector columns preferably run parallel to the axis of rotation 14. The detector rows are located in planes perpendicular to the axis of rotation and in this embodiment are arranged in an arc of a circle about the radiation source S (focus-centered detector). In other embodiments, however, they may also be shaped differently, e.g. describe an arc of a circle about the axis of rotation 14 or be rectilinear. Each detector element that is struck by the bundle of rays 4 supplies in each position of the radiation source location a measured value for a ray of the bundle of rays 4.

The opening angle of the bundle of rays 4, designated $\alpha_{max}$, determines the diameter of the object cylinder within which the object to be examined is located during the acquisition of the measured values. In this case, the opening angle is defined as the angle enclosed by a ray lying in a plane perpendicular to the axis of rotation 14 at the edge of the bundle of rays and a plane running through the radiation source S and the axis of rotation 14.

The examination area 13 or the object or the patient table may be displaced by means of a motor 5 parallel to the axis of rotation 14 or the z axis. However, in an equivalent manner, the gantry may also be displaced in this direction. In this example of embodiment, the X-ray source has a focal spot that can be moved parallel to the axis of rotation, from which focal spot the X-rays come. The radiation source location can thus be displaced parallel to the axis of rotation.

Figure 2:
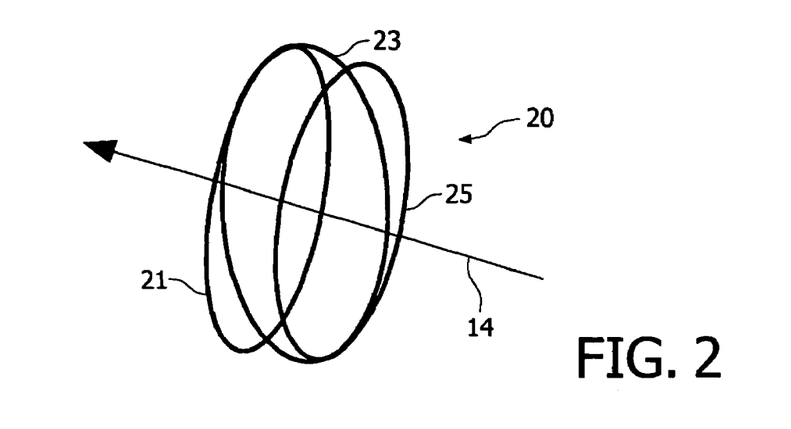
FIG. 2 shows an overall trajectory according to the invention on which the radiation source location can move relative to the examination area.
Figure 3:
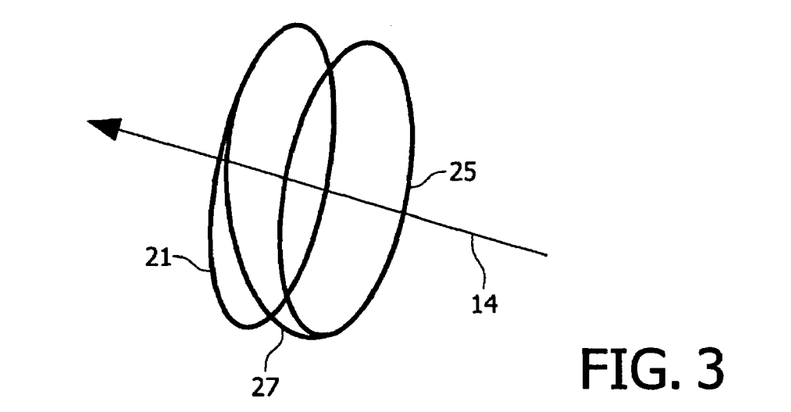
FIG. 3 shows a further overall trajectory according to the invention on which the radiation source location can move relative to the examination area.
Figure 4:
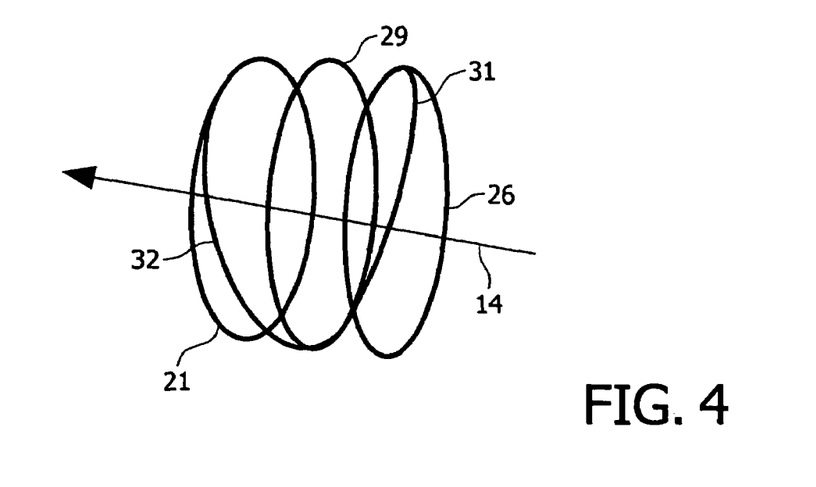
FIG. 4 shows a further overall trajectory on which the radiation source location can move relative to the examination area.

By means of the motors 2, 5 and the movable focal spot, the radiation source S and the focal spot of the X-ray source and the detector unit 16 can describe an overall trajectory 20 relative to the examination area 13, which overall trajectory runs on an imaginary cylindrical surface. Examples of such overall trajectories are shown in FIGS. 2 to 4. According to the invention, there is a first closed partial trajectory 21, at least one second closed partial trajectory 25, 26, 29 and at least one third partial trajectory 23, 27, 31, 32 which connects the first partial trajectory 21 and the at least one second partial trajectory 25, 26, 29 to one another. The first partial trajectory 21 and the at least one second partial trajectory 25, 26, 29 are arranged around the axis of rotation 14.

In FIG. 2, two circular first and second partial trajectories 21, 25 with the same diameter and the same axis of rotation 14 are connected by a third elliptical partial trajectory 23.

In FIG. 3, two circular partial trajectories 21, 25 with the same axis of rotation 14 and the same diameter are connected to one another by an ellipse section 27. A further overall trajectory according to the invention is shown in FIG. 4, in which three circular partial trajectories 21, 26, 29 with the same diameter and the same axis of rotation 14 are connected to one another by in each case one of the ellipse sections 31, 32.

For each point in the examination area 13 between the first partial trajectory 21 and the at least one second partial trajectory 25, 26, each plane containing the respective point intersects the overall trajectory at least once. A set of measured values which has been acquired while the radiation source location B has moved relative to the examination area 13 along the overall trajectory 20 is therefore complete, since the respective point in the examination area has been irradiated from at least one of the respective points of intersection. A reconstruction of the part of the examination area 13 which is located between the circular partial trajectories 21 and 25, 26 is thus possible using exact reconstruction methods.

During the acquisition of the measured values, in this example of embodiment the heart movement is recorded by an electrocardiograph 8 in a known manner. For this purpose, the chest area of a patient is connected to the electrocardiograph 8 via electrodes (not shown). In other embodiments, particularly in the case of other moving objects, the movement of the object may be monitored in other ways. For instance, the movement information could for example be obtained from the values measured by the detector unit 16 themselves, so that there is no need to record the movement by means of an additional device such as an electrocardiograph. For this purpose, a kymogram is first created from the measured values, and the movement can be derived from said kymogram in a known manner. A detailed description of this method can be found in "Kymogram detection and kymogram-correlated image reconstruction from subsecond spiral computer tomography scans of the heart", M. Kachelrieβ, D. A. Sennst, W. Maxlmoser, W. A. Kalender, Medical physics 29 (7): 1489-1503, 2002, to which reference is hereby made. Of course, the computer tomography method according to the invention can also be carried out when there is no periodically moving object in the examination area 13.

In this example of embodiment it is assumed that the patient is not breathing during the measurement. The breathing movement can thus be ignored. Otherwise, the breathing movement could be measured, for example, by means of a deformable chest strap which is connected to a known breathing movement measurement device.

The measured values acquired by the detector unit 16 are fed to a reconstruction computer 10 which is connected to the detector unit 16 for example via a contactless data transmission system (not shown). Moreover, an electrocardiogram is transmitted from the electrocardiograph 8 to the reconstruction computer 10. The reconstruction computer 10 reconstructs a CT image of the examination area 13, in particular an absorption distribution, and displays it for example on a monitor 11. The two motors 2 and 5, the reconstruction computer 10, the radiation source S, the electrocardiograph 8 and the transfer of the measured values from the detector unit 16 to the reconstruction computer 10 are controlled by the control unit 7. Moreover, the control unit 7 controls transmission of the electrocardiogram from the electrocardiograph 8 to the reconstruction computer 10.

Figure 5:
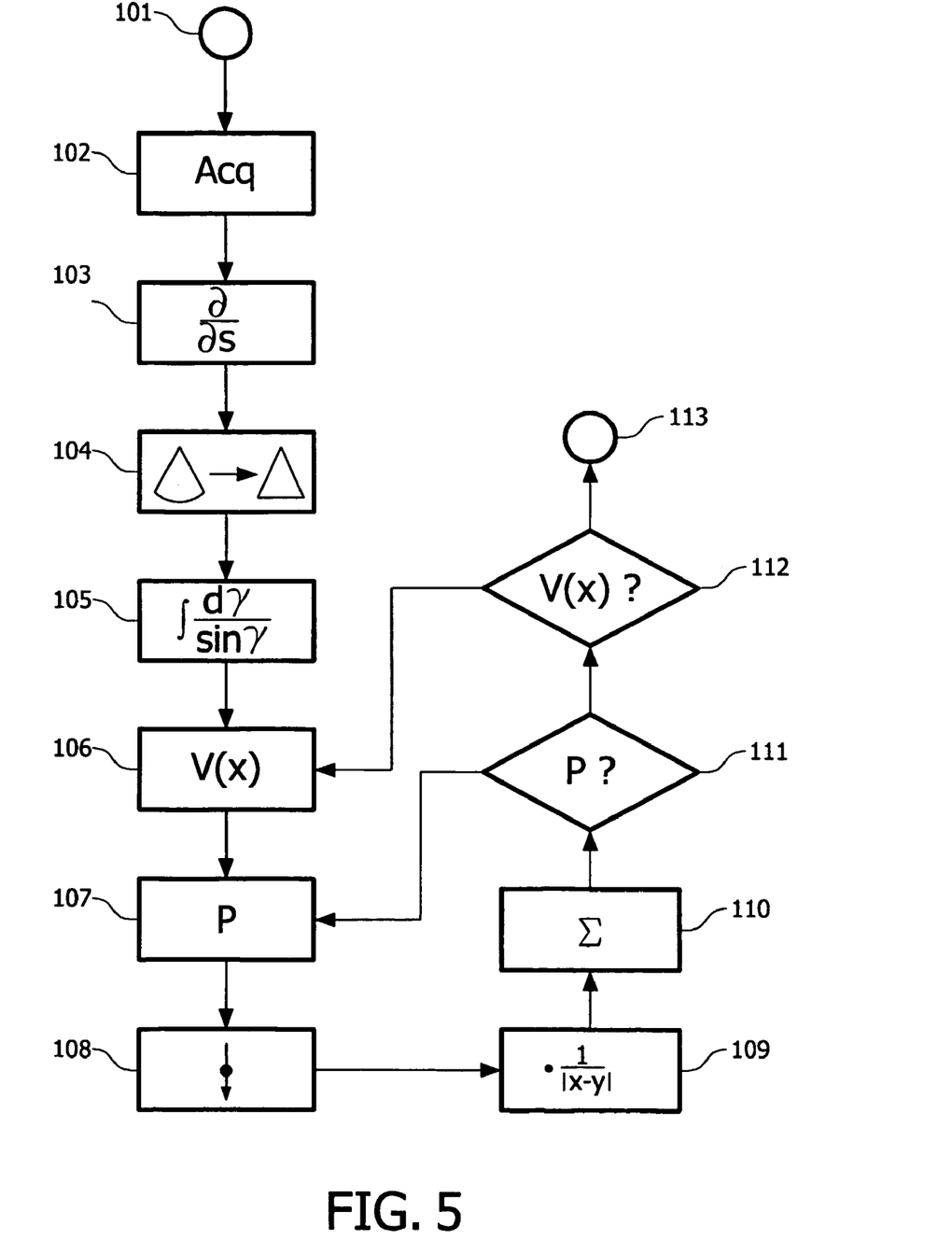
FIG. 5 shows a flowchart of the method according to the invention.

FIG. 5 explains the sequence of a measurement and reconstruction method according to the invention which can be carried out using the computer tomography scanner shown in FIG. 1.

Following initialization in step 101, the gantry 1 rotates at an angular velocity which in this example of embodiment is constant. However, it may also vary, for example as a function of time or of the radiation source position or of the position of the radiation source location.

In step 102, the radiation of the radiation source S is switched on and the radiation source location is moved relative to the examination area 13 along the overall trajectory 20 by moving the patient table or the focal spot. At the same time as or even before the radiation source S is switched on, the electrocardiograph 8 is activated so that an electrocardiogram is recorded at the same time as the measured values are being acquired.

During the acquisition of the measured values, the distance between the first partial trajectory 21 and the second partial trajectory 25 is selected such that the object to be reconstructed can be arranged completely in the part of the examination area which is delimited by these two partial trajectories 21, 25, since, as already mentioned above, the acquired data record is complete only in respect of this part. Moreover, this distance should be selected such that the projections of the first partial trajectory 21 and of the second partial trajectory 25 along the rays emitted by the radiation source S fall on the detector unit. This means that the distance between these two partial trajectories 21 and 25 and/or the extent of the detector unit in the direction of the axis of rotation 14 should be selected such that the part 33 of the cone-shaped bundle of rays 4 shown by way of example in FIG. 6, said part being delimited by the two partial trajectories 21, 25, is completely detected by the detector unit 16.

Figure 6:
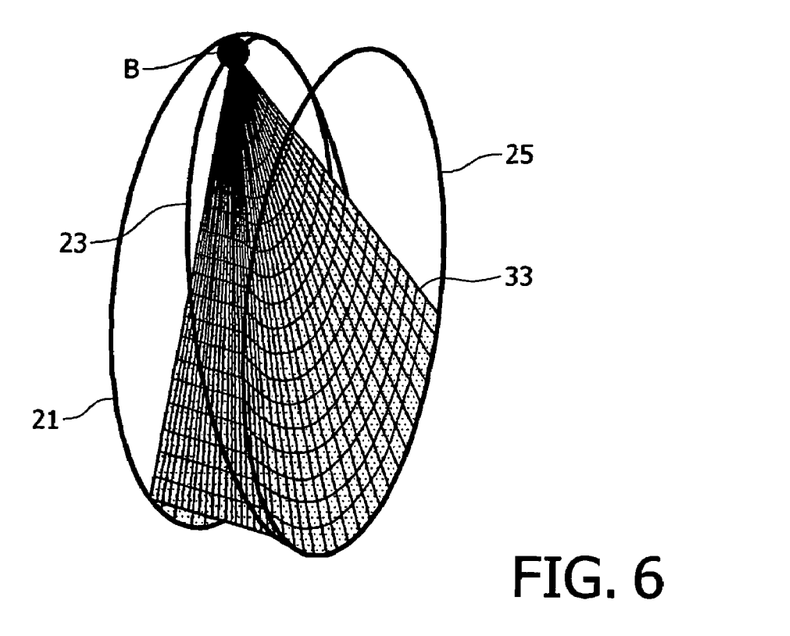
FIG. 6 shows an overall trajectory according to the invention with a radiation source location and a bundle of rays.
Figure 7:
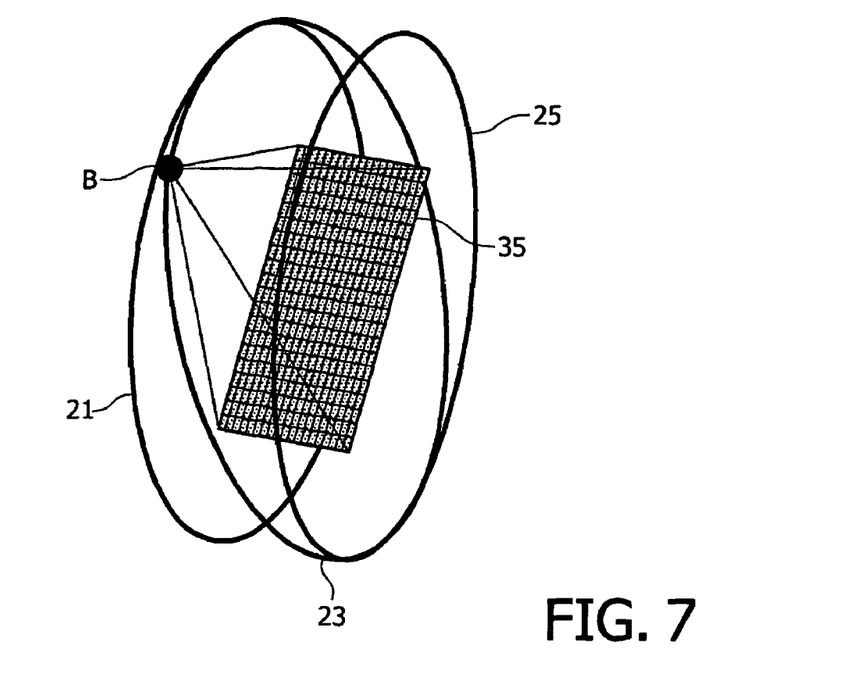
FIG. 7 shows an overall trajectory with a radiation source location and a virtual, planar detector surface.

In other words, only the part 33 of the cone-shaped bundle of rays 4 which is delimited by the partial trajectories 21 and 25 is required for complete acquisition, regardless of whether the partial bundle 33 or the bundle of rays 4 comes from the first or the second partial trajectory 21, 25 or from the third partial trajectory 23. The computer tomography scanner could therefore have a dynamic collimator which during the acquisition always collimates only the partial bundle 33, in order to avoid subjecting the object to be examined to unnecessary radiation exposure.

If in other embodiments there are a number of second partial trajectories, in each case only the part 33 of the cone-shaped bundle of rays 4 which is delimited by two adjacent partial trajectories of the first and second partial trajectories is required for complete acquisition.

In this example of embodiment it is assumed that rest phases, in which the object moves relatively little, and movement phases, in which the object moves a great deal, alternate in the periodically moving object. In the case of the heart, this rest phase is the diastolic phase. If the object is in a rest phase, the radiation of the radiation source S is switched on and measured values are acquired. If, on the other hand, the object is in a movement phase, the radiation of the radiation source S is switched off so that no measured values are acquired. The radiation source S is in this way controlled by the control unit 7, to which the electrocardiogram is continuously transmitted by the electrocardiograph 8.

If a temporally precise switching on and off of the radiation source is technically problematic, so that acquisition of the measured values when the object is in a rest phase is not possible, the radiation source is controlled such that at least the majority, in particular more than 80% or 90%, of the measured values are acquired while the object is in a rest phase, so that measured values are essentially acquired only in the rest phases.

As an alternative, the measured values may be acquired independently of the object movement, although in this case only measured values acquired while the object was in a rest phase are taken into account in the reconstruction described below.

In this example of embodiment, at first neither the patient table nor the focal spot moves, so that the radiation source S, or more precisely the radiation source location B, moves relative to the examination area along the first partial trajectory 21. The radiation source location B rotates along this partial trajectory 21 until measured values have been acquired during one or more rest phases of the object over as large an angular range as possible. Preferably, the radiation source S moves on the partial trajectory 21 until measured values which correlate with the one or more rest phases of the object have been acquired over the entire angular range of 360°. When the desired amount of measured values have been acquired along the first partial trajectory, the patient table or focal spot of the X-ray source is moved parallel to the axis of rotation 14, so that the radiation source location advances relative to the examination area 13 along an ellipse 23. In this case, the gantry 1 may furthermore rotate at a constant angular velocity without the rotation movement having to be accelerated or slowed down. The overall trajectory 20 according to the invention can therefore be realized relatively easily with known computer tomography scanners. While the radiation source location is moving relative to the examination area 13 along the third partial trajectory 23 also, measured values are acquired only when the object is in a rest phase. The radiation source location moves on this ellipse 23 until measured values have been acquired over as large an angular range as possible, in particular over the entire angular range of 360°, along the partial trajectory 23. Once the desired amount of measured values has been acquired during the movement of the radiation source location along the ellipse 23, the patient table and focal spot move so that the radiation source location is guided along the third partial trajectory 23 toward the second partial trajectory 25. Once the radiation source location has reached the second partial trajectory 25, the patient table and focal spot end their movement parallel to the axis of rotation, so that the radiation source location is now moving along the second partial trajectory 25. In this case, too, the measured values are acquired only when the object is in a rest phase, and measurement is continued until measured values have been acquired over as large an angular range as possible along the second partial trajectory 25, in particular over an angular range of 360°.

For the computer tomography method according to the invention, the sequence in which the partial trajectories are passed through is not important. The measured values could therefore also be acquired, for example, first along the second partial trajectory 25 or along the third partial trajectory 23.

If measured values are acquired a number of times from one and the same position of the radiation source location, these measurement values which are redundant per se may be used to increase the signal-to-noise ratio. For this purpose, measured values whose rays come from the same position of the radiation source location and strike the same detector element may be averaged, for example arithmetically, to form one measured value.

Once the measured values have been acquired, a CT image is reconstructed from these measured values. This could take place for example using a known iterative reconstruction method. In this case, starting from a predefined initial distribution of absorption values in the examination area, an iteration step may comprise the following steps: a) simulating the acquisition along the overall trajectory to produce a simulated set of measured values; b) difference formation between the simulated and the corresponding measured values that were actually measured; c) back-projection of the differences along the rays belonging to the respective differences and measured values into the examination area. Such methods are known, for example, by the name "Algebraic Reconstruction Technique (ART)" ("Principles of Computerized Tomographic Imaging", Chapter 7: Algebraic Reconstruction Algorithms, Kak, Slaynay, IEEE Press New York, 1988).

In this example of embodiment, the reconstruction is carried out using a filtered back-projection. For this purpose, in step 103 the measured values are firstly partially differentiated. This partial derivative is explained in more detail below.

The first partial trajectory 21, $y_1$, and the second partial trajectory 25, $y_2$ can be described by the following equations:

$$y_1(s_1) = \begin{pmatrix} R\cos s_1 \\ R\sin s_1 \\ 0 \end{pmatrix} \text{ and } y_2(s_2) = \begin{pmatrix} R\cos s_2 \\ R\sin s_2 \\ z_0 \end{pmatrix}. \quad (1)$$

Here, the vectors $y_1(s_1)$ and $y_2(s_2)$ describe the course of the first and second partial trajectories 21, 25, wherein these vectors point from a reference point, located on the axis of rotation 14 at the point $z=0$, to the radiation source location on the corresponding partial trajectory. The point $z=0$ is the point at which the trajectory plane of the first partial trajectory 21 and the axis of rotation 14 intersect. The angular positions $s_1$ and $s_2$ in each case assume values of between 0 and $2\pi$. The variable R denotes the radius of the first 21 and second 23 circular partial trajectories, and $z_0$ is the z position at which the trajectory plane of the second partial trajectory 25 and the axis of rotation 14 intersect. The elliptical third partial trajectory 23 can be described by the following equation:

$$y_3(s_3) = \begin{pmatrix} R\cos(s_3) \\ R\sin(s_3) \\ z_0\sin^2(s_3/2) \end{pmatrix}. \quad (2)$$

The angular position $s_3$ of the ellipse 23 may assume values of between 0 and $2\pi$. If instead of a complete ellipse only an ellipse section 27 is used as the third partial trajectory, then the angular position $s_3$ assumes a correspondingly smaller range of values. For instance, in the case of a half ellipse as shown in FIG. 3, for example, the angular position s assumes values of between 0 and $\pi$.

For each radiation source location on one of the partial trajectories $y_1(s_1)$, $y_2(s_2)$ and $y_3(S_3)$, the respectively associated measured values $D_f(y_i(s_i),\theta)$ can be described by $$D_f(y_i(s_i), \theta) = \int_0^\infty dl f(y_i(s_i) + l\theta). \quad (4)$$

Here, the index i assumes the values 1, 2 and 3, and $\theta$ is a unit vector which points in the different ray directions of the rays coming from the respective radiation source location. The function $f(x)$ denotes the absorption value at the point x in the examination area 13. The partial derivative in step 103 can then be described by the following equation:

$$D'_f(y_i(s_i), \theta) = \frac{\partial D_f(y_i(s_i), \theta = const.)}{\partial s_i}. \quad (5)$$

Parallel rays which come from different positions of the radiation source location are therefore differentiated on the basis of the angular position $s_i$ of the radiation source location B. For this purpose, measured values whose rays run parallel and come from the same partial trajectory but from different radiation source locations can be combined to form in each case one group. The measured values of a group are in each case differentiated on the basis of the angular position $s_i$ of the radiation source location on the respective partial trajectory. This derivative may be carried out, for example, using a Fourier transform or the finite element method.

Once the measured values have been differentiated, in step 104 they are projected along the respective rays onto a virtual, planar detector surface 35. The virtual detector surface 35 contains the axis of rotation 14 and rotates with the radiation source S about the axis of rotation 14. That is to say, a ray of the radiation source S is always perpendicular on the axis of rotation 14 and the virtual detector surface 35. In this example of embodiment, the virtual detector surface 35 does not move in the direction of the axis of rotation 14 and is selected to be so large that all the rays of the bundle of rays 33 shown in FIG. 6 and described above penetrate the virtual detector surface 35. The size of the virtual detector surface 35 must therefore be selected such that all the rays which come from one point on the overall trajectory 20 and pass through the examination area and leave through the region delimited by the partial trajectories 21 and 25 are detected. In this example of embodiment this detector surface 35 is rectangular.

The differentiated measured values projected onto the virtual detector surface 35 are then filtered in step 105. The filter lines and directions along which the measured values are filtered on the detector surface 35 depend on which partial trajectory 21, 23, 25 the radiation source location was located during acquisition of the respective measured value, in which direction it is moving on this partial trajectory and on the position of the measured value on the virtual detector surface 35.

In order to determine the respective filter lines, the detector surface 35 is divided into a number of regions with the aid of projections of the first partial trajectory 21 and second partial trajectory 25 along the rays coming from the respective radiation source location.

Figure 8:
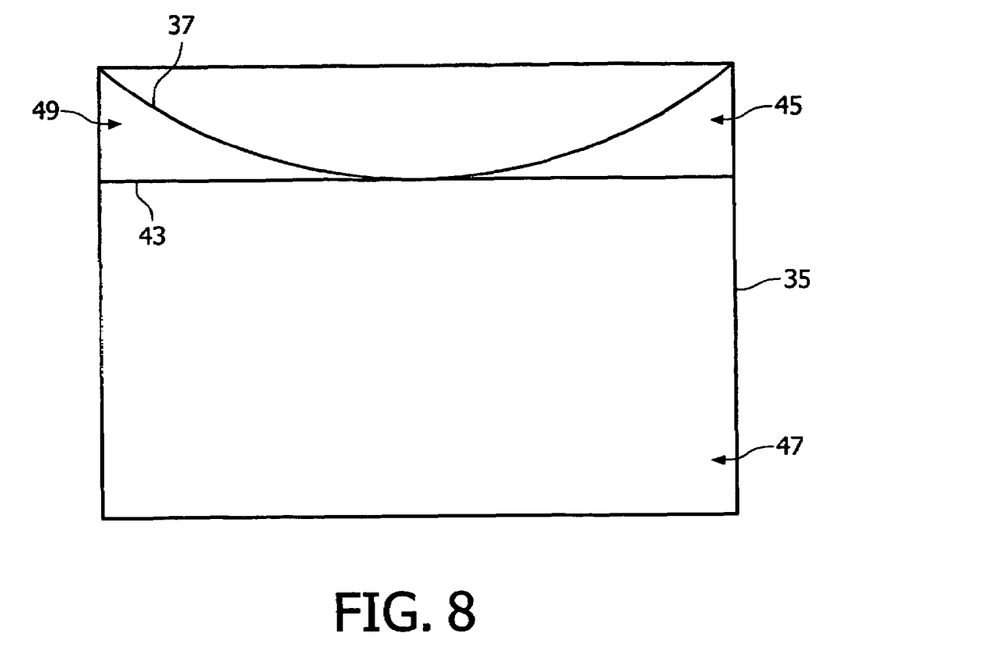
FIG. 8 shows the virtual, planar detector surface onto which the second partial trajectory is projected, viewed from a point on a first partial trajectory.
Figure 9:
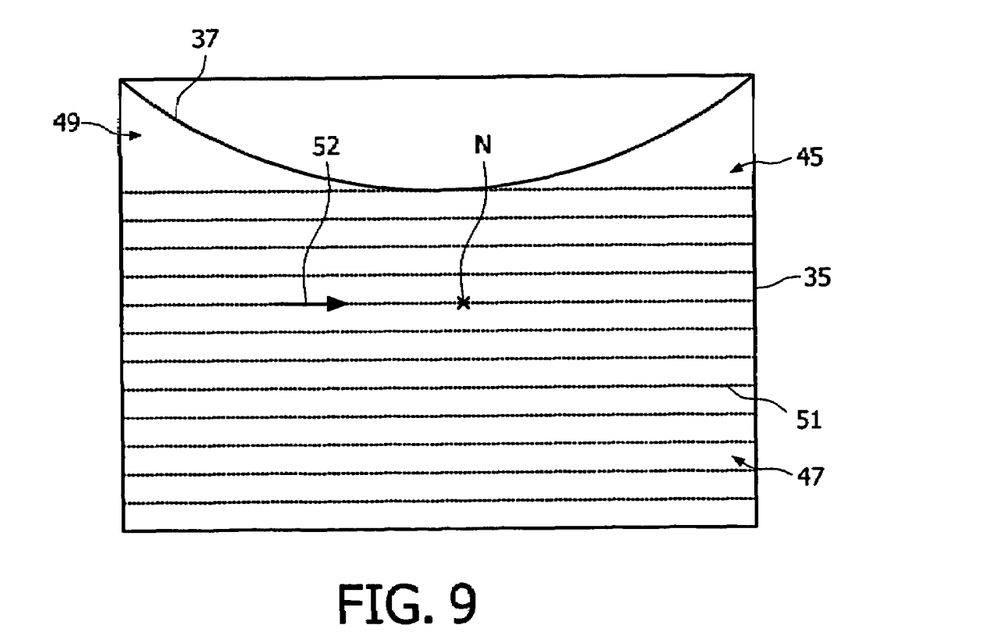
FIGS. 9-11 show the virtual, planar detector surface onto which the second partial trajectory is projected, with filter lines and directions, viewed from a point on the first partial trajectory.

In order to determine filter lines and filter directions for measured values whose rays come from the first partial trajectory 21, the detector surface 35 is divided into three regions 45, 47, 49 by the projection 37 of the second partial trajectory 25 onto the detector surface 35 along the rays coming from the first partial trajectory 21 and by a straight line 43 which contacts this projection 37 at a tangent at one point and runs perpendicular to the axis of rotation 14. These regions are shown in FIG. 8. In this figure and also in FIGS. 9 to 13, in each case the virtual detector surface 35 can be seen, wherein the direction from left to right in these figures corresponds essentially to the direction in which the radiation source location advances. More precisely, the direction from left to right corresponds to the component of the advance movement of the radiation source location which is oriented perpendicular to the axis of rotation.

When, in the text which follows, a measured value lies or is arranged in a certain region on the virtual detector surface 35, this means that the measured value originally acquired by the detector unit 16 has been projected into this region in step 104.

A filter line 51 (FIG. 9) is assigned to a measured value D whose ray comes from the first partial trajectory 21 and which lies in the region 47 delimited by the straight line 43, said filter line running through this measured value and parallel to the straight line 43 and perpendicular to the axis of rotation 14. These filter lines 51 are shown together with their filter directions 52, wherein the filter directions 52 in FIG. 9 point from left to right, that is to say essentially in the advance movement direction of the radiation source location.

Figure 10:
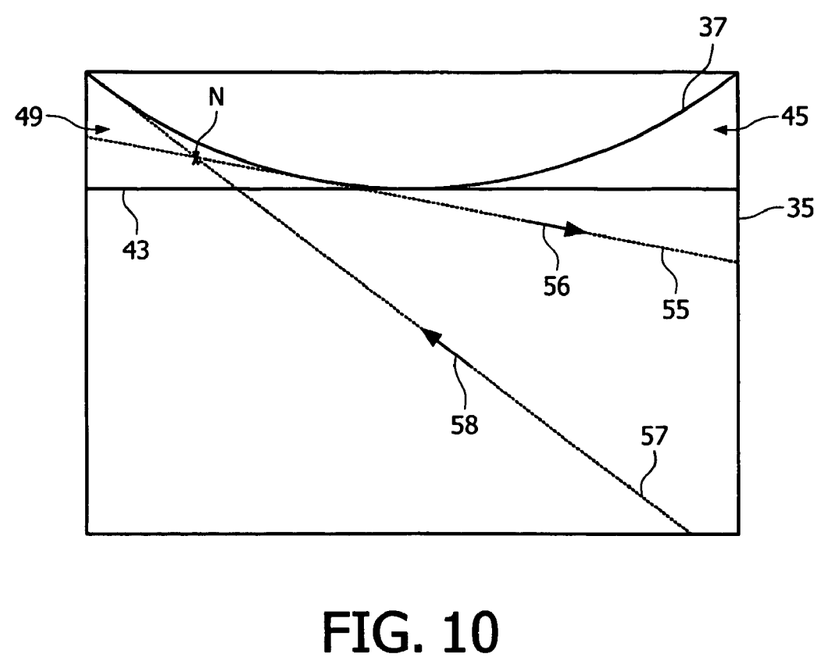
Figure 11:
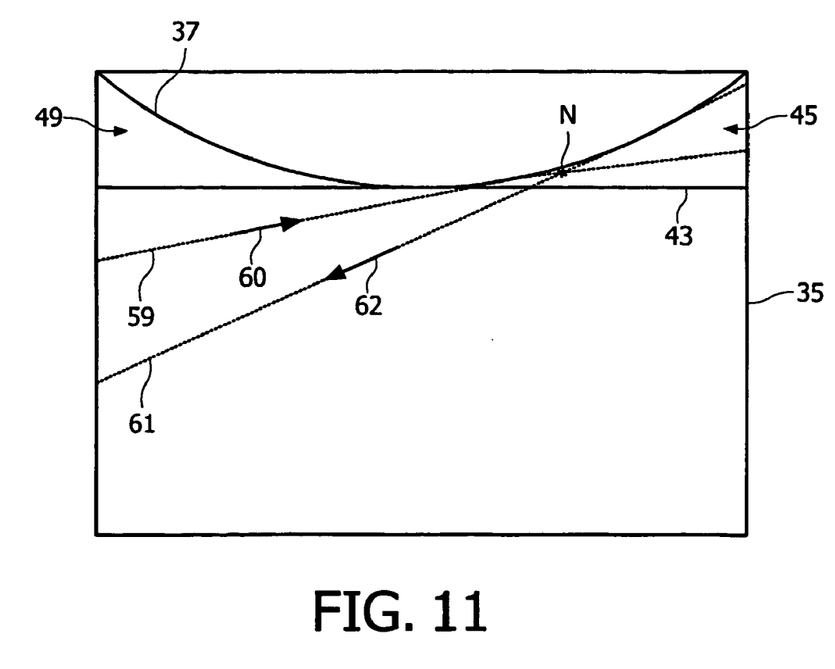

Two filter lines 55, 57 or 59, 61 are assigned to a measured value D whose ray comes from the first partial trajectory and which lies in one of the regions 45, 49 that are delimited by the straight line 43 and the projection 37 of the second partial trajectory 25, said filter lines in each case running at a tangent to the projection 37 (cf. FIG. 10 and FIG. 11). The two tangents of the projection 37 are therefore assigned as filter lines 55, 57 or 59, 61 to such a measured value D, said filter lines running through this measured value D.

The filter directions 56, 58 and 60, 62 belonging to these filter lines 55, 57 and 59, 61 are likewise shown in FIG. 10 and FIG. 11. A filter line 57 of a measured value arranged in the left-hand region 49, which touches the projection 37 to the left of the measured value to be filtered, has a filter direction 58 which points essentially from right to left, that is to say in the direction opposite the advance movement direction of the radiation source location. If a filter line 55 of the same measured value touches the projection 37 to the right of said measured value, the corresponding filter direction in FIG. 10 points from left to right. A filter line 59 of a measured value arranged in the right-hand region, which touches the projection 37 to the left of this measured value, has a filter direction 60 which points essentially from left to right. A filter line 61 which runs through the same measured value but whose point of contact with the projection 37 lies to the right of this measured value is assigned a filter direction 62 which runs from right to left.

As an alternative, all measured values whose rays come from the first partial trajectory 21, regardless of their arrangement on the planar, virtual detector surface 35, could be filtered along filter lines which run perpendicular to the axis of rotation 14. That is to say, in FIG. 9, the filter lines 51 and filter directions 52 would then be distributed over the entire detector surface 35. The use of these filter lines, which is described in more detail below, is of course possible only when measured values are arranged along the filter lines. The opening angle of the cone-shaped bundle of rays 4 must therefore be selected to be so large that measured values are acquired and arranged also in the region of the virtual detector surface that is delimited by the projection 37 and the upper edge of the detector surface 35.

The filter lines and filter directions of those measured values whose rays come from the second partial trajectory 25 correspond to the filter lines and filter directions for measured values whose rays come from a radiation source position on the first partial trajectory 21. That is to say, in order to obtain the corresponding filter lines and filter directions for these measured values, in FIGS. 8 to 11 the projection 37, the filter lines and the filter directions must be reflected on a horizontal axis which runs centrally over the detector surface 35. The corresponding transfer of the above explanations regarding the filter lines and filter directions for measured values whose rays come from a radiation source location on the first partial trajectory 21 to measured values whose rays come from a radiation source location on the second partial trajectory 25 leads to the corresponding filter lines and filter directions.

Figure 12:
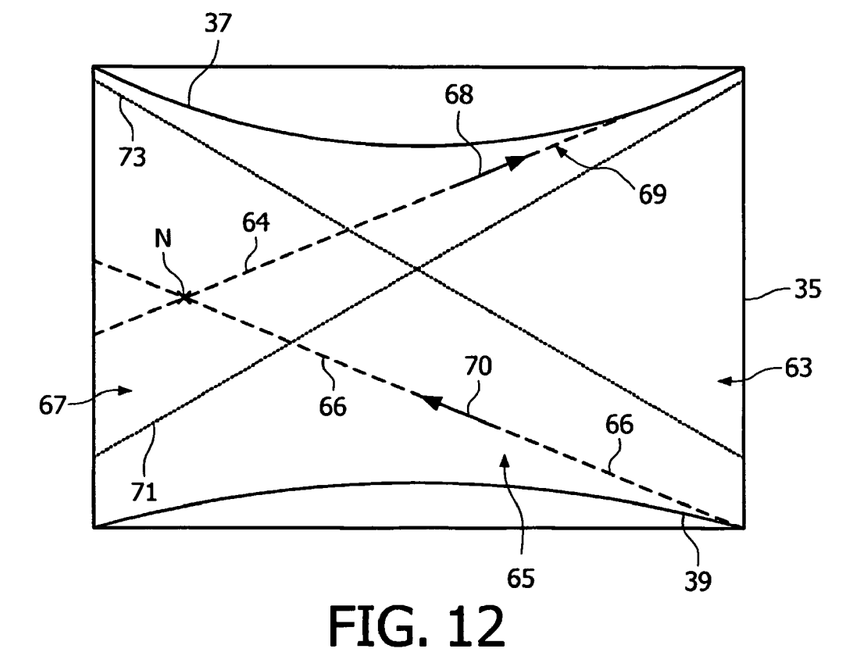
FIG. 12 shows the virtual, planar detector surface onto which the first and second partial trajectories are projected, with filter lines and directions, viewed from a point on a third partial trajectory.

The filter lines and filter directions for measured values whose rays come from the elliptical third partial trajectory 23 are described with reference to FIG. 12. This figure shows the projection 37 of the second partial trajectory 25 along the rays coming from the respective radiation source location onto the virtual, planar detector surface 35 and the corresponding projection 39 of the first partial trajectory 21. Furthermore, FIG. 12 shows two dashed lines 71, 73 which each run at a tangent to the two projections 37, 39. These two dashed lines 71, 73 divide the region delimited by the projections 37, 39 into four regions 63, 65, 67, 69. Two filter lines are assigned to each measured value, the course and filter direction of said filter lines depending on the position of the respective measured value on the detector surface 35.

For measured values whose rays come from a radiation source position on the elliptical third partial trajectory 23, there are two sets of filter lines, in each case one filter line from each set being assigned to each measured value. Filter lines of the first set run, for a measured value D which lies in the regions 67 or 69, at a tangent to the projection 37 of the second partial trajectory 25 onto the detector surface 35, with the point of contact of this filter line 64 lying to the right of the respective measured value 80 in FIG. 12. If, on the other hand, the measured value lies in one of the regions 63 or 65, then the filter line of the first set runs at a tangent to the projection 39 of the first partial trajectory 21 onto the detector surface 35, with the point of contact of this filter line with the projection 39 lying to the left of the measured value in FIG. 12. The filter directions of the filter lines of the first set in FIG. 12 run essentially from left to right for measured values whose rays come from the section of the third partial trajectory 23 on which the radiation source location moves in the direction of the second partial trajectory 23. For measured values whose rays come from the section of the third partial trajectory 23 on which the radiation source location moves in the direction of the first partial trajectory 21, the filter directions of the filter lines of the first set run essentially from right to left.

For a measured value which is arranged in the regions 69 or 63 on the detector surface 35, the filter line of the second set runs at a tangent to the projection 37, with the point of contact of this filter line with the projection 37 in FIG. 12 lying to the left of the measured value. If a measured value is located in one of the regions 65 or 67, then the filter line of the second set runs at a tangent to the projection 39, with the point of contact of this filter line 66 with the projection 39 being to the right of the measured value. The filter directions of the filter lines of the second set run from right to left for measured values whose rays come from the section of the third partial trajectory 23 on which the radiation source location moves in the direction of the second partial trajectory 25. In FIG. 12 they run from left to right for measured values whose rays come from the section of the third partial trajectory 23 on which the radiation source location moves in the direction of the first partial trajectory 21.

Figure 13:
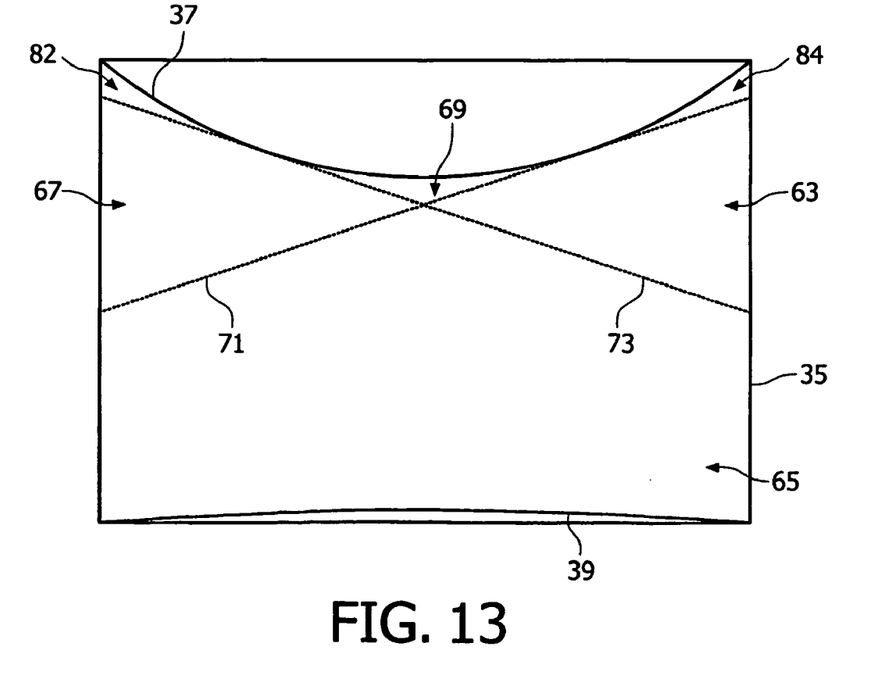
FIG. 13 shows the virtual, planar detector surface onto which the first and second partial trajectories are projected, viewed from a point on the third partial trajectory.

If the radiation source location is located on the elliptical third partial trajectory 23 in the vicinity of one of the two other partial trajectories 21, 25, or if the detector is very wide, as shown in FIG. 13 measured values may be arranged in regions 82, 84, which lie between the projections 37, 39, but not in one of the regions 63, 65, 67, 69. The measured values which lie in these regions 82, 84 are in this example of embodiment not taken into account in the filtering and backprojection.

If the overall trajectory has a number of second partial trajectories 26, 29, as shown in FIG. 4 for example, each part of the examination area 13 that is delimited by two adjacent partial trajectories selected from the first and second partial trajectories can then be considered individually, with the method according to the invention being carried out for each of these parts. That is to say, in step 105, in the case of one first partial trajectory 21 and two second partial trajectories 26 and 29, two virtual detector surfaces 35 may be defined which are each passed through by the bundle of rays delimited by the adjacent partial trajectories 21, 29 and 29, 26. The respectively adjacent partial trajectories 21, 29 or 29, 26 are then projected onto each of these virtual detector surfaces 35 and then, as described above, filter lines and filter directions can be defined on the respective virtual detector surface.

In another embodiment, if there are a number of second partial trajectories 26, 29, just one virtual detector surface may be defined, the size of which is selected such that all the rays which come from the overall trajectory pass through the examination area 13 and leave the examination area 13 between the first partial trajectory 21 and the second partial trajectory 26 which is furthest from the first partial trajectory 21, and penetrate the detector surface. Furthermore, if there are a number of second partial trajectories 26, 29, the course of the filter lines and filter directions, as described above, may be determined using the projection of the second partial trajectory 26 furthest from the first partial trajectory 21 and of the first partial trajectory 21 onto the virtual detector surface.

In the reconstruction of the CT image described below, this choice of filter lines and filter directions according to the invention leads to a particularly good image quality.

The filtering may be carried out in accordance with the following equation:

$$P(y_i(s_i), \beta(y_i(s_i), x)) = \quad (6)$$

-continued $$\mu \sum_{n=1}^{N_f} \int_{-\pi}^{\pi} \frac{d\gamma}{\sin\gamma} D'(y_i(s_i), \beta(y_i(s_i), x)\cos\gamma + e_n(y_i(s_i), x)\sin\gamma).$$

Here, $P(y_i(s_i), \beta(y_i(s_i), x))$ is the respectively filtered measured value whose ray comes from $y_i(s_i)$ and runs through the point x in the examination area 13. The vector $\beta(y_i(s_i), x)$ points from the respective radiation source location $y_i(s_i)$ to the point x in the examination area and is defined by $$\beta(y_i(s_i), x) = \frac{x - y_i(s_i)}{|x - y_i(s_i)|} \quad (7)$$

The redundancy factor $\mu$ may take account of redundancies arising during filtering or reconstruction. Examples of possible redundancy factors are mentioned below. The summation over n takes into account a different number $N_f$ of filter lines from measured value to measured value. Moreover, $e_n(y_i(s_i), x)$ is a vector which describes the course of the respective filter line and is defined by the following equation:

$$e_n(y_i(s_i), x) = \frac{(\beta(y_i(s_i), x) \times r_n(y_i(s_i), x)) \times \beta(y_i(s_i), x)}{|(\beta(y_i(s_i), x) \times r_n(y_i(s_i), x)) \times \beta(y_i(s_i), x)|}. \quad (8)$$

Here, the vector $r_n(y_i(s_i), x)$ points in the respective filter direction.

Furthermore, $\gamma$ is the κ angle which will be described below.

Hereinbelow, a filtering operation according to the invention which is based on equation (6) and is carried out along the above-described filter lines will be described.

In order to filter a measured value along a filter line assigned to this measured value, the measured values on this filter line are in each case multiplied by two weighting factors and summed in the filter direction.

The first weighting factor decreases as the sine of the κ angle increases. In particular, it is equal to the reciprocal value of the sine of the κ angle. The κ angle is the angle between the ray belonging to the measured value that is to be filtered and the ray belonging to the respective measured value that is to be multiplied by the first weighting factor and lies on the filter line.

In order to avoid singularity of the first weighting factor at the point at which the κ angle is equal to zero, by way of example the filtered measured values may in each case be determined at points on the virtual detector surface which lie between the measured values lying on the filter line.

Furthermore, each measured value lying on the respective filter line is multiplied by a second weighting factor which is equal to the κ angle distance dγ or Δγ between two adjacent measured values lying on the filter line. Preferably, the measured values are arranged on a filter line in an equidistant manner so that the κ angle distance between two adjacent measured values is constant for a filter line. If the κ angle distances between a measured value and the two adjacent measured values are different, then the κ angle distance in the filter direction can be taken as the weighting factor for example, or else the weighting factor can be determined by arithmetic averaging of the two κ angle distances.

If in other embodiments the κ angle distance is the same for all filter lines, the multiplication by the second weighting factor could be omitted.

The summation of the weighted measured values lying on the respective filter line is repeated for all filter lines of a measured value, so that for one measured value a number of sums equal to the number of filter lines is determined. For instance, for a measured value whose ray comes from the first partial trajectory 21 and which lies in the region 47 in FIG. 9, the result is just one sum of weighted measured values lying on the filter line, since only one filter line is assigned to this measured value. In this example of embodiment, two filter lines are assigned to a measured value which lies for example in the region 49 on the detector surface 35 in FIG. 8 or FIG. 10, so that after filtering two corresponding sums are produced for this measured value. If a number of such sums are produced for a measured value, they are then added in accordance with equation (6). The resulting sum is then multiplied by a redundancy factor and finally forms the filtered measured value.

The redundancy factor depends on which radiation source location belongs to the respective measured value and where the measured value is arranged on the virtual detector surface.

If the ray belonging to a measured value comes from the first partial trajectory 21, then the redundancy factor is ½ when the measured value is arranged in the region 47 in FIG. 8, and is ¼ when the measured value is arranged in one of the regions 45 or 49 in FIG. 8.

The same applies in respect of measured values whose rays come from the second partial trajectory 25, wherein, as already described above, the virtual detector surface 35 in FIG. 8 has to be reflected along a horizontal axis that is arranged centrally on the detector surface, in order to obtain the corresponding regions 45, 47 and 49.

If the ray belonging to a measured value comes from the third partial trajectory 23, then the redundancy factor for this measured value is ¼.

If the third trajectory forms only a half-ellipse, as shown in FIG. 3, then the redundancy factor for rays which come from the third trajectory is ½.

The multiplication by the weighting factors and the summation or filtering of the measured values in accordance with equation (6) may be carried out in a known manner using a Fourier transform.

Once all the measured values on the virtual, planar detector surface 35 have been filtered along the filter lines assigned to them, the filtered measured values are used to reconstruct the absorption distribution in the examination area by means of a back-projection. The back-projection can be described by the following equation:

$$f(x) = \frac{-1}{2\pi^2} \sum_{i=1}^{3} \int \frac{ds}{|x - y_i(s_i)|} P(y_i(s_i), \beta(y_i(s_i), x)). \quad (9)$$

Here, $f(x)$ denotes the value to be reconstructed, in particular the absorption value, at the point x in the examination area. The following back-projection is carried out in accordance with equation (9).

First, in step 106 a voxel V(x) is determined within a predefinable field of view FOV in the examination area 13 between the first partial trajectory 21 and the second partial trajectory 25.

Then, in step 107, a radiation source location which has not yet been taken into account in this back-projection is selected on the overall trajectory (or a projection). A projection is in this connection the set of all the rays which come from a radiation source location. A specific radiation source location is selected only if the part 33 (FIG. 6) of the cone-shaped bundle of rays 4 coming from this radiation source location that is delimited by the two adjacent first and second partial trajectories 21, 25 passes through the voxel V(x).

If a periodically moving object is located in the examination area 13 and if in step 102 the measured values have been acquired continuously, that is to say independently of the respective movement phases of the object, then in this step 107 only projections which have been acquired during a rest phase of the object should be selected. This may be done with the aid of the electrocardiogram recorded by the electrocardiograph 8. Even if in step 102 projections have been acquired only during rest phases of the object, this can be checked in step 107 by means of the electrocardiogram, that is to say a check can be made as to whether the projections have actually been acquired during the rest phases of the object. Projections which have not been acquired during a rest phase may continue to be disregarded in the following back-projection.

If not enough measured values to form a complete data set have been acquired in the rest phase, measured values which have been acquired during a movement phase or have been determined by known interpolation methods may also be taken into account.

In step 108, a check is made as to whether there is, in the projection selected in step 107, a measured value whose ray runs through the center of the voxel V(x). If such a measured value or ray cannot be found, the point at which a central ray would strike the detector surface 35 is determined. The associated measured value is then calculated by interpolating the measured values of adjacent rays.

The measured value which can be assigned to the ray passing through the voxel, or the measured value obtained by interpolation, is multiplied in step 109 by a weighting factor which becomes smaller as the distance of the radiation source location from the voxel position x in the FOV increases, and in particular is selected to be proportional to the reciprocal value of this distance or equal to said reciprocal value.

In step 110, the measured value multiplied by this weighting factor is added to the voxel V(x). Initially, all voxels V(x) are set to the same initial value, for example to the value 0.

In step 111, a check is made as to whether all the projections which can be taken into account for the back-projection, as mentioned above in relation to step 107, have been considered. If this is not the case, the flowchart branches to step 107. Otherwise, it continues with step 112.

In step 112, a check is made as to whether all voxels V(x) in the FOV have been passed through. If this is not the case, the method continues with step 106. If, on the other hand, all voxels V(x) in the FOV have been passed though, then the absorption in the entire FOV has been determined and the reconstruction method is terminated (step 113).

LIST OF REFERENCES $\alpha_{max}$ opening angle of the cone-shaped bundle of rays
B radiation source location
D measured value
S radiation source
1 gantry
2, 5 motor
3 collimator arrangement
4 cone-shaped bundle of rays
7 control unit
8 electrocardiograph
10 reconstruction computer
11 monitor
13 examination area
14 axis of rotation
16 detector unit
20 overall trajectory
21 first partial trajectory
25, 26, 29 second partial trajectory
23, 27, 31, 32 third partial trajectory
33 part-bundle of the cone-shaped bundle of rays
35 virtual detector surface
37 projection of a second partial trajectory onto the virtual detector surface
39 projection of the first partial trajectory onto the virtual detector surface
43 straight line at a tangent to the projection and perpendicular to the axis of rotation
45, 47, 49, 63, 65, 67, 69 regions on the virtual detector surface
51, 55, 57, 59, 61, 64, 66 filter lines
52, 56, 58, 60, 62, 68, 70 filter directions
71, 73 lines running at a tangent to the projections 37, 39
82, 84 regions on the virtual detector surface

The invention claimed is:

1. A computer tomography method, comprising:
producing a cone-shaped bundle of rays by means of a radiation source, said bundle of rays passing through an examination area and coming from a radiation source location,
producing a relative movement between the radiation source location on the one hand and the examination area on the other hand along an overall trajectory, wherein the relative movement comprises a rotation about an axis of rotation along a first, closed partial trajectory, a rotation about the axis of rotation along at least one second, closed partial trajectory and a movement along at least one third partial trajectory which connects the first and the at least one second partial trajectories to one another, wherein the third partial trajectory is a non-circular, elliptical trajectory,
acquiring measured values which depend on the intensity in the bundle of rays on the other side of the examination area, by means of a detector unit during the relative movement,
reconstructing a CT image of the examination area from the measured values.

2. A computer tomography method as claimed in claim 1, wherein the first and second trajectories are circular trajectories.

3. The computer tomography method as claimed in claim 1, wherein the first and second partial trajectories in each case form a circle having the same diameter.

4. The computer tomography method as claimed in claim 1, wherein the reconstruction is carried out using a filtered back-projection.

5. The computer tomography method as claimed in claim 4, wherein the filtered back-projection comprises the following steps:
determining a partial derivative of the measured values, wherein in each case measured values whose assigned rays are parallel to one another are partially differentiated on the basis of the angular position of the radiation source location on the respective trajectory from which the respective ray comes,
filtering of the measured values along filter lines, the filtering of a measured value, comprising:

assigning one or more filter lines to the measured value, with a filter direction being assigned to each filter line, multiplying measured values which lie on a filter line assigned to the measured value by a respective weighting factor which is proportional to the reciprocal value of the sine of a respective angle which is enclosed between a ray which belongs to the measured value to be filtered and a ray which belongs to the respective measured value to be multiplied by the weighting factor, adding all the measured values multiplied by a weighting factor along each filter line of the measured value in the filter direction, so that a sum is produced for each filter line, adding the sums to form a filtered measured value, back-projection of the differentiated and filtered measured values.

6. The computer tomography method as claimed in claim 5, wherein the filtering of a measured value is carried out on a virtual, planar detector surface which rotates with the radiation source and onto which all the measured values of the respective part of the cone-shaped bundle of rays delimited by two adjacent partial trajectories selected from the first and the at least one second partial trajectory are projected along the respective rays, wherein the filter lines assigned to the measured value run on the virtual detector surface perpendicular to the axis of rotation or at a tangent to the projection of a section of the two adjacent partial trajectories selected from the first and at least one second partial trajectory.

7. The computer tomography method as claimed in claim 1, wherein in the examination area there is a periodically moving object in which rest phases, in which the object movement is relatively small, and movement phases, in which the object movement is relatively large, alternate, wherein the object is a heart and the rest phase is the diastolic phase, and wherein measured values are essentially acquired only when the object is in one of its rest phases, wherein measured values are acquired until the radiation source locations on the first, the at least one second and the at least one third partial trajectory that belong to the acquired measured values have in each case scanned a predefined angular range or predefined angular ranges.

8. The computer tomography method as claimed in claim 1, wherein a dynamic collimator arrangement collimates the cone-shaped bundle of rays such that for each radiation source location on the overall trajectory the cone-shaped bundle of rays is delimited by two adjacent partial trajectories selected from the first and the at least one second partial trajectory.

9. The computer tomography scanner, for carrying out the method as claimed in claim 1, having a radiation source for producing a bundle of rays that passes through an examination area, a drive arrangement for rotating an object in the examination area and the radiation source relative to one another about an axis of rotation and allowing them to move parallel to the axis of rotation, a detector unit for acquiring measured values, said detector unit being coupled to the radiation source, a reconstruction unit for reconstructing a CT image from the measured values, a control unit configured to control the radiation source, the detector unit, the drive arrangement and the reconstruction unit in accordance with the following steps:

producing a cone-shaped bundle of rays by means of the radiation source, said bundle of rays passing through an examination area and coming from a radiation source location, producing a relative movement between the radiation source location on the one hand and the examination area on the other hand along an overall trajectory, wherein the relative movement comprises a rotation about an axis of rotation along a first, closed partial trajectory, a rotation about the axis of rotation along at least one second, closed partial trajectory and a movement along at least one third partial trajectory which connects the first and the at least one second partial trajectories to one another, wherein the third partial trajectory is a non-circular ellipse, acquiring measured values which depend on the intensity in the bundle of rays on the other side of the examination area, by means of the detector unit during the relative movement, reconstructing a CT image of the examination area from the measured values.

10. The computer tomography scanner as claimed in claim 9, wherein the radiation source has a radiation source location that can be displaced parallel to the axis of rotation in that the radiation source is an X-ray source with a focal spot that can be displaced parallel to the axis of rotation.

11. The computer tomography scanner as claimed in claim 9, wherein the computer tomography scanner additionally has a recording device for recording the movement of an object, wherein the recording device includes an electrocardiograph for recording a movement of the heart.

12. The computer tomography scanner as claimed in claim 9, wherein the computer tomography scanner additionally has a dynamic collimator arrangement which is adapted such that for each radiation source location on the overall trajectory the cone-shaped bundle of rays is delimited by two adjacent partial trajectories selected from the first and the at least one second partial trajectory.

13. The computer tomography method of claim 1, further including moving the radiation source along at least a fourth, closed partial trajectory and at least a fifth closed elliptical trajectory, wherein the fifth closed elliptical trajectory connects the second and the fourth, closed partial trajectories together.

14. A computer readable medium embodied with a computer program, which when executed by a computer, carries out the acts of:

producing a cone-shaped bundle of rays by means of a radiation source, said bundle of rays passing through an examination area and coming from a radiation source location, producing a relative movement between the radiation source location on the one hand and the examination area on the other hand along an overall trajectory, wherein the relative movement comprises a rotation about an axis of rotation along a first, closed partial trajectory, a rotation about the axis of rotation along at least one second, closed partial trajectory and a movement along at least one third closed trajectory which connects the first and the at least one second partial trajectories to one another, wherein the third closed trajectory is elliptical, acquiring measured values which depend on the intensity in the bundle of rays on the other side of the examination area, by means of a detector unit during the relative movement, reconstructing a CT image of the examination area from the measured values.

15. The computer readable medium of claim 14, wherein the first and second trajectories are circular.

16. A computer tomography scanner, comprising:
a radiation source that rotates about an examination region and generates radiation that traverses the examination region;
a detector array that detects radiation that traverses the examination region; and
a control unit that controls the radiation source;
wherein the radiation source is configured to move along a first trajectory with respect to an object in the examination region, a second trajectory with respect to an object in the examination region, and a third elliptical trajectory with respect to an object in the examination region, wherein the third elliptical trajectory connects the first and second trajectories together, and the third elliptical trajectory defines an ellipse with unequal foci.

17. The computer tomography scanner of claim 16, wherein the first and second trajectories are circular.

18. The computer tomography scanner of claim 16, wherein the first and second trajectories are closed, partial circular trajectories.

19. The computer tomography scanner of claim 16, wherein the radiation source is configured to move along at least a fourth circular trajectory with respect to an object in the examination region and at least a fifth elliptical trajectory with respect to an object in the examination region, wherein the fifth elliptical trajectory connects the second and the fourth circular trajectories together.

20. The computer tomography scanner of claim 19, wherein the first, second and fourth trajectories are closed, partial circular trajectories.

* * * * *